United States Patent
Edgren et al.

(10) Patent No.: US 7,060,734 B1
(45) Date of Patent: Jun. 13, 2006

(54) PHARMACEUTICAL COATING COMPOSITION AND METHOD OF USE

(75) Inventors: David E. Edgren, El Granada, CA (US); Shu Li, Newark, CA (US); Patrick S.-L. Wong, Palo Alto, CA (US); Gurdish Bhatti, Fremont, CA (US); Liang-Chang Dong, Sunnyvale, CA (US); Si-Hong Yum, Belmont, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/721,111

(22) Filed: Nov. 22, 2000

Related U.S. Application Data

(63) Continuation of application No. 09/129,687, filed on Aug. 5, 1998, now abandoned.
(60) Provisional application No. 60/058,264, filed on Sep. 9, 1997.

(51) Int. Cl.
*A01N 25/00* (2006.01)

(52) U.S. Cl. ............... 514/781; 514/772.7; 514/975; 525/398; 525/403
(58) Field of Classification Search ............ 424/480, 424/463, 484, 488, 495; 514/975, 781, 772.7; 525/398, 403
See application file for complete search history.

(56) References Cited

U.S. PATENT DOCUMENTS

| | | | |
|---|---|---|---|
| 2,799,241 A | 7/1957 | Wurster | ............ 118/240 |
| 3,845,770 A | 11/1974 | Theeuwes | ............ 128/260 |
| 3,916,899 A | 11/1975 | Theeuwes | ............ 128/260 |
| 3,961,041 A | 6/1976 | Nishimura et al. | |
| 4,063,064 A | 12/1977 | Saunders et al. | ............ 219/121 |
| 4,088,864 A | 5/1978 | Theeuwes | ............ 219/121 M |
| 4,117,182 A * | 9/1978 | Andrews | |
| 4,160,452 A | 7/1979 | Theeuwes | |
| 4,200,098 A | 4/1980 | Ayer et al. | ............ 128/260 |
| 4,285,987 A | 8/1981 | Ayer et al. | ............ 427/3 |
| 4,327,725 A | 5/1982 | Cortese et al. | ............ 128/260 |
| 4,329,451 A * | 5/1982 | Zweigle | |
| 4,948,593 A | 8/1990 | Wright et al. | |
| 5,601,845 A | 2/1997 | Buxton et al. | |

FOREIGN PATENT DOCUMENTS

| | | |
|---|---|---|
| EP | 0 077 956 | 5/1983 |
| EP | 0 339 811 A | 11/1989 |
| EP | 0 459 516 A | 12/1991 |
| GB | 2 258 613 A | 2/1973 |
| GB | 2 258 810 A | 2/1993 |

OTHER PUBLICATIONS

Remington's "Pharmaceutical Sciences", 14th Ed., p 1681, (1970). J.A. Pharm. Assoc., vol. 48, pp 451–454, (1959) and ibid, vol. 49, pp 82–84, (1960).
Modern Plastics Encyclopedia, vol. 46, pp 62–70 (1969).
Pharmaceutical Science, by Remington, 14th Ed., pp 1626–1678 (1970) published by Mack Publishing Co., Easton, Pa.

* cited by examiner

*Primary Examiner*—Edward J. Webman
(74) *Attorney, Agent, or Firm*—David Abraham

(57) ABSTRACT

A composition is disclosed comprising a polymer and a surfactant in a solvent exhibiting a common solubility for the polymer and the surfactant. The composition provides a dosage form for administering a drug over time.

7 Claims, 4 Drawing Sheets

PHARMACEUTICAL COATING COMPOSITION AND METHOD OF USE

CROSS-REFERENCE TO RELATED APPLICATION

This application is a continuation of application Ser. No. 09/129,687 filed Aug. 5, 1998, now abandoned, which claims the benefits of provisional application U.S. Ser. No. 60/058,264 filed Sep. 9, 1997 under 35 U.S.C. §119(e).

FIELD OF THE INVENTION

This invention pertains to a novel and useful pharmaceutical coating composition. More particularly, the invention related to a pharmaceutically acceptable composition comprising at least one polymer and at least one surfactant which composition with a single solvent can be coated onto a dosage form. The invention concerns also a process of coating a dosage form with the composition and the solvent.

BACKGROUND OF THE INVENTION

In Remington's *Pharmaceutical Sciences*, 14th, Ed., p 1681, published in 1970, it was reported that pill coating has been a pharmaceutical technique for well over ten centuries. For example, Rhazes (850–932 A.D.) used mucilage, a seaweed substance, for coating pills in the ninth century, and Avicenna (980–1037 A.D.) is credited with the introduction of silver and gold pill coatings into medicine. The coating of pills with finely powdered talcum, called pearl coating, was popular in previous times. Gelatin coating of pills was introduced into medicine by Garot in 1838. The first sugar-coated pills in the United States were imported from France in about 1842. The first sugar-coated pill was manufactured in the United States in 1856 by Warner, a Philadelphia pharmacist. In about 1884 Unna introduced enteric coated pills.

Unique pharmaceutically-acceptable tablets, manufactured as an osmotic dosage form entered the fields of medicine and pharmacy with the invention of osmotic dosage forms by inventors Theeuwes and Higuchi in U.S. Pat. Nos. 3,845,770 and 3,916,899. The osmotic dosage forms disclosed in these patents comprise a semipermeable membrane that surrounds a compartment containing a therapeutic agent. The membrane is permeable to the passage of an external fluid, and it is impermeable to the passage of drug. There is at least one exit through the membrane for delivering the therapeutic agent from the osmotic dosage form.

A pioneering advancement in osmotic dosage forms was made available to the drug dispensing arts in U.S. Pat. No. 4,327,725 by patentees Cortese and Theeuwes. The invention provided by these inventors concerned an osmotic dosage form for delivering a therapeutic agent, that because of its solubility, is difficult to deliver in therapeutic amounts at a controlled rate over time. The dosage form of U.S. Pat. No. 4,327,725 comprises a semipermeable wall that surrounds a therapeutic agent and an expandable agent. In operation, the expandable agent in the presence of imbibed fluid, expands and pushes the therapeutic agent through an exit passageway from the dosage form.

While the above presented dosage forms are useful for the management of health and disease, a serious disadvantage is associated with their manufacture. That is, the prior art used two or more solvents to dissolve a coating-forming membrane and a flux enhancer, because one solvent does not dissolve both the membrane and the flux enhancer. A typical solvent system used by the prior ad for this purpose comprises two or more organic solvents, often possessing degrees of unknown incompatibility. Further, the prior art solvents often produced high-flux membranes that exhibited mechanical defects, which lead to weakened membranes accompanied by brittleness. Then too, the use of multiple solvent can produce haziness or opacity in a membrane, which makes it impossible to identify selected regions of a dosage form. Also, the use of multiple organic solvents presents an environmental problem as the solvents require complicated recover systems to avoid contaminating the environment, which recovery systems are expensive to install and to operate.

It will be appreciated by those skilled in the drug dispensing art, that if a coating is provided that comprises a single solvent and its substantively-free of excessive organic solvent for coating dosage forms, such a coating and its accompanying solvent would have an immediate positive value, and concomitantly, represent an advancement in the drug coat and drug coating art. Likewise, it will be appreciated by those versed in the coat and process-coating arts, that if a coat and a process for coating are made available for dosage forms that overcome the disadvantages known to the prior art, they would have a practical application in the fields of medicine and pharmacy.

OBJECTS OF THE INVENTION

Accordingly, in view of the above presentation, it Is an immediate object of this invention to provide a novel and useful coating composition for dosage forms, and which coating composition overcomes the disadvantages associated with the prior art.

Another object of this invention is to provide a new coating composition comprising pharmaceutically acceptable ingredients, and which coating composition is innocuous and useful for manufacturing a dosage form.

Another object of this invention is to provide a nontoxic coating composition, which coating composition is useful for making dosage forms.

Another object of this invention is to provide a coating composition comprising a membrane and a surfactant, which coating composition is capable of being applied to a dosage form without difficulty and is applied at relative lower cost.

Another object of this invention is to provide a composition comprising a membrane and a surfactant, and a common solvent for the membrane and the surfactant.

Another object of the invention is to provide a coating composition characterized by simplicity of formulation, ease of manufacture and a single solvent system that can be use to form a coating solution that avoids binary or tertiary solvent systems.

Other objects, features and advantages of this invention, will be more apparent to those versed in the dispensing art from the following detailed specification taken in conjunction with the drawings and the accompanied claims.

BRIEF DESCRIPTION OF THE DRAWINGS

In the drawing figures, which are not drawn to scale, but are set forth to illustrate various embodiments of the inventory, the drawing figures are as follows.

Drawing

Drawing

Drawing

Drawing

In the drawing figures and in the specification, like parts in related figures are identified by like numbers. The terms appearing earlier in the specification and in the description of the drawing figures, as well as in embodiments thereof, are further described elsewhere in this disclosure.

DETAILED DESCRIPTION OF THE INVENTION

Figure 1:
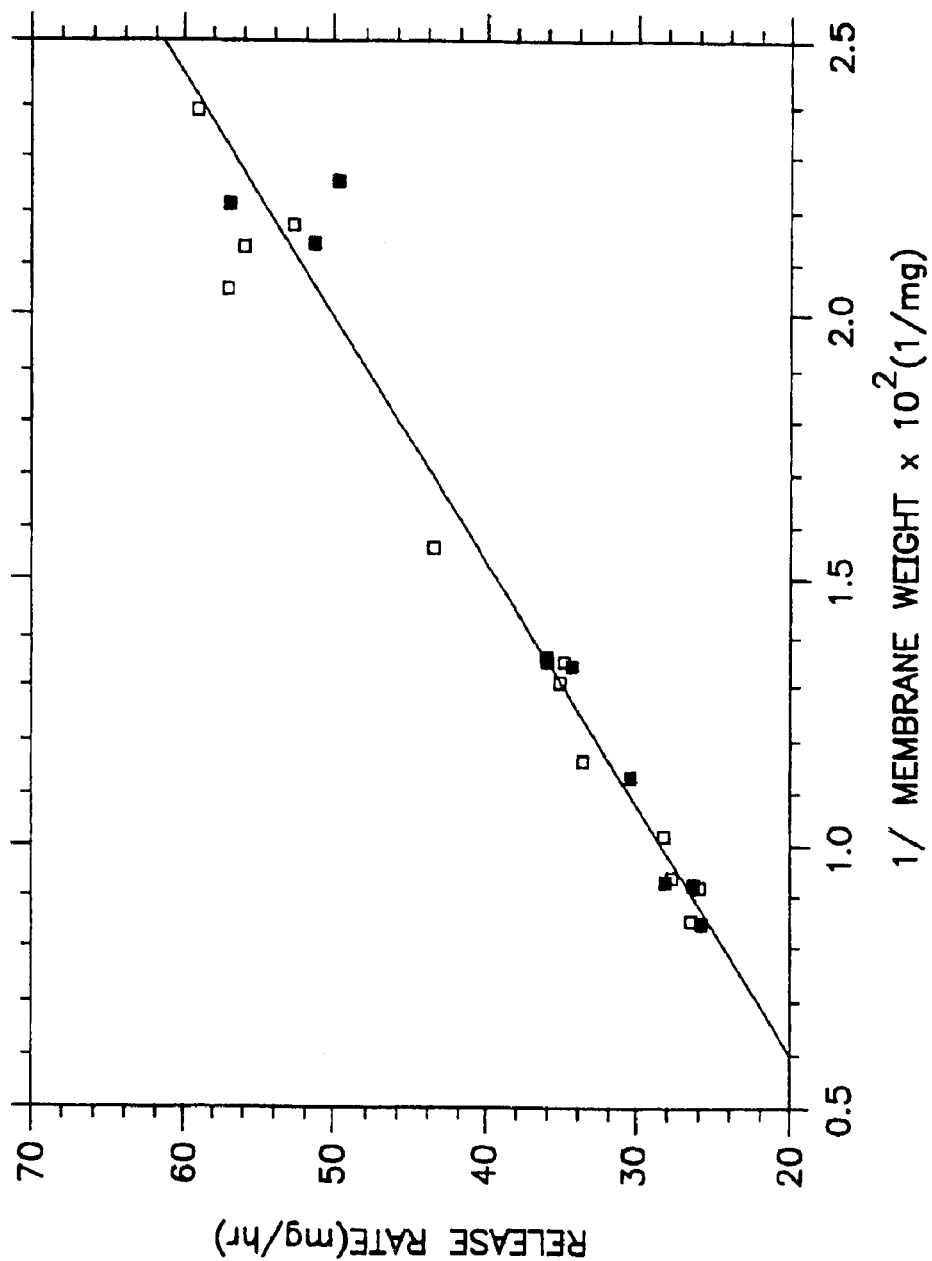
FIG. 1 depicts the release rate vs the reciprocal membrane weight for two coating conditions.

In accordance with the practice of this invention, a therapeutic agent, including a drug, is coated with a composition comprising a polymer and a surfactant. The polymer in the process of coating the therapeutic agent coverts to a membrane that surrounds the therapeutic agent to yield a dosage form. The polymer is nontoxic, and it does not adversely affect an animal host, including a human, and a therapeutically-acceptable drug. The polymers useful for providing a membrane comprise a member selected from the group consisting of cellulose ester, cellulose ether, and cellulose ester-ether. Representative of specific polymers comprise a member selected from the group consisting of cellulose acylate, cellulose diacylate, cellulose triacylate, cellulose acetate, cellulose diacetate, and cellulose triacetate, and ethylcellulose. The amount of polymer on a weight based in a coating composition in a final, dry coated membrane is 40 wt % to 99.5 wt %.

In coating composition comprising the polymer also comprises one or more pharmaceutically acceptable surfactants. The surfactant generally for the purpose of this invention is amphiphilic as it contains both a hydrophobic and a hydrophilic group. Representative of surfactants that exhibit solubility in aqueous and nonaqueous solvents are polyoxyethylene fatty acid esters that includes polyoxyethylene monostearate, polyoxyethylene sorbitan monopalmitate, polyoxypropylene glycols that include polyoxypropylene glycol having a molecular weight of 950 and 3 moles to 85 moles of ethylene oxide, polyoxypropylene glycol possessing a molecular weight of 1200 and 7 to 40 moles of ethylene glycol, polyoxypropylene glycol possessing a mole weight of 1750 and 5 moles to 160 moles of ethylene oxide, polyoxypropylene glycol having a molecular weight of 2050 and 10 moles to 110 moles of ethylene oxide, polyoxypropylene glycol having a 2250 molecular weight and 5 moles to 200 moles of ethylene oxide, polyoxypropylene glycol possessing a molecular weight of 2750 and 15 to 250 moles of ethylene oxide, and polyoxypropylene glycol of 3250 molecular weight and 8 moles to 300 moles of ethylene glycol. The amount of surfactant in a composition for coating is 0.5 wt % to 60 wt %.

Other pharmaceutically acceptable surfactants for the purpose of this invention include triblock copolymers of ethylene oxide-propylene oxide, ethylene oxide, which include polymers with an average molecular weight of 2200 and 3 to 20 moles of ethylene oxide, polymers with molecular weight 8,600 and 50 to 110 moles of ethylene oxide, polymers with molecular weight of 7800 and 45 to 80 moles of ethylene oxide, polymers with 15,000 molecular weight and 110 to 170 moles of ethylene oxide, and those with molecular weight 12,200 and 70 to 130 moles of ethylene oxide.

Other pharmaceutically acceptable surfactants-suitable for use in this invention include monoglycerides, diglycerides, sorbitan fatty acid esters, polyoxyethylene sorbitan fatty acid esters, polyoxyethylene sorbitol esters, polyoxyethylene esters of acids, polyoxyethylene alcohols, polyoxyethylene glyceride ester, polyoxyethylene-oxypropylene monostearate with 10 to 40 moles of ethylene oxide, polyoxyethylene alkyl amine, ionic surfactants such as N-cetyl-ethyl morpholinium ethosulfate, N-soya-n-ethyl morpholinium ethosulfate, alkyl aryl sulfonate, polyoxyethylene ether, polyoxyethylene glyceride alkyl aryl sulfonate blend, polybxyethylene alkyl aryl ether-alkyl aryl sulfonate blend, nonionic-anionic blends, and polyethylene sorbitol oleate-polyoxyethylene amine blend.

The composition for providing the coating composition comprises of 0 wt % to 30 wt % of a surfactant polymer of hydroxypropylcellulose of 7,500 to 150,000 weight average molecular weight, and 0 wt % to 30 wt % of a polyvinylpyrrolidone of 1,200 to 225,000 viscosity average molecular weight. A coloring agent, a colorant, or opacifying agent can be added to the composition to identify the dosage form. The colorant should b pharmaceutically acceptable as represented by FD & C Red No. 3, FD & C Red No. 40, FD & C Yellow No. 5, FD & C Yellow No. 6, FD & C Blue No. 1, FD & C Blue No. 2, FD & C Green No. 5, and iron oxides including black, yellow and red iron oxides. The opacifying agent should be pharmaceutically acceptable such as finely-divided titanium dioxide. The amount of colorant or opacifying agent in a composition is 0 wt % to 3.5 wt %.

Optionally, other functional excipients can be formulated within the coating composition such as anti-tack agents to improve coating quality and ease of processing. Anti-tack agents can be incorporated within the coating single-solvent composition In dissolved form or in the dispersed form. Anti-tack agents are formulated at zero to five weight percent based on the drug weight of the coating composition. These agents include glycerol fatty acid esters such as glycerol monostearate, fats of glycerides of saturated C12 to C18 fatty acids, esters of medium chain fatty acids such as, coconut oil, palm kernal oil, babassu oil, finely divided silicon dioxide, silica aluminates, talc, precipitated silicas, fumed silicas, metal fatty acids such as magnesium stearate, fatty acids saturated C12 to C18 such as stearic acids, and saturated C12 to C18 alcohol such as stearyl alcohol.

The dosage form, when manufactured as an osmotic dosage form with controlled-release properties comprises at least one exit in the dosage form membrane. The phase controlled-release as used herein, indicates that control is exercised over both the duration and the profile of the drug-release pattern. The expression passageway, as used for the purpose of this invention, includes aperture, orifice, bore, pore, porous element through which the drug can be pumped, diffuse, travel or migrate, a hollow fiber, capillary tube, porous overlay, porous insert, microporous member, and porous composition. The expression also includes a compound that erodes or is leached from the membrane in the fluid environment of use to produce at least one passageway in dosage form. Representative compounds suitable for forming at least one passageway, or a multiplicity of passageways, includes an erodible poly(glycolic) acid or poly(lactic) acid member in the wall; a gelatinous filament; a water-removable poly(vinyl alcohol); leachable compounds such as fluid removable pore-forming polysaccharides, acid, salts, or oxides. A passageway or a plurality of passageways can be formed by a leaching a compound such as sorbitol, sucrose, lactose, fructose, or the like, from the membrane to provide a controlled-release dimensioned pore-passageway. The passageway can have any shape such as round, triangular, square, elliptical, and the like, for assisting in the controlled-metered release of drug from dosage form. Dosage form can be constructed with one or passageways in spaced apart relation to one or more surfaces of a dosage form. Passageway and equipment for forming passageways are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled releasing dimension, sized, shaped and adapted as a releasing-pore formed by aqueous leaching to provide a releasing-pore formed by aqueous leaching to provide a releasing-pore of controlled release-rate are disclosed in U.S. Pat. No. 4,200,098 by Ayer and Theeuwes; and in U.S. Pat. No. 4,285,987 by Ayer and Theeuwes.

The membrane is manufactured and applied in one process, comprises an air suspension process. This procedure consists in suspending and tumbling a compressed drug core comprising a single layer or a bilayer core, in a current of air and wall forming composition until a wall is applied to the core. The air suspension procedure is well-suited for independently forming the wall. The air suspension procedure is described in U.S. Pat. No. 2,799,241; *J. A. Pharm. Assoc.*, Volume 48, pages 451 to 454, (1959); and ibid, Volume 49, pages 82 to 84, (1960).

The dosage form can be coated in an air suspension coat, or by other membrane forming techniques such as pan-coating systems, wherein membrane forming compositions are deposited by successive spraying of the composition on the drug-core compartment, accompanied by tumbling in a rotating pan. Finally, the membrane coated compartments are dried in a forced air over at 30° C. to 50° C. for up to a week to free dosage form 10 of solvent. Generally, the membrane formed by these techniques have a thickness of 1 to 30 mils (0.254 mm to 0.762 mm, with a presently preferred thickness of 4 to 10 mils, 0.101 mm to 0.254 mm).

The dosage form of the invention is manufactured by standard manufacturing techniques. For example, in one manufacture the drug and other core-forming ingredients comprising a single drug layer or bilayer core facing the exit means are blended and pressed into a solid layer, or a solid bilayer. The drug and other ingredients can be dry-blended or blended with a solvent and mixed into a solid or semisolid formed by conventional methods such as ball-milling, calendaring, stirring, roll-milling or churning and then pressed into a preselected shape. The layer possesses dimensions that correspond to the internal dimensions of the area the layer is to occupy in the dosage form and in a bilayer it also possesses dimensions corresponding to the second layer for forming a contracting arrangement therewith. Next, in a bilayer core, the push layer is placed in contact with the drug layer. The push layer is manufactured using techniques for providing the drug layer. The layering of the drug layer and the push layer can be fabricated by convention press-layering techniques. Finally, a single layer or the two layer compartment, the layer or layers are surrounded with a membrane. A passageway is laser, leached, or mechanically drilled through the membrane to contact the drug layer. When the passageway is formed by a laser, the dosage form is optically-oriented automatically by the laser equipment for forming the passageway on the preselected surface for forming the passageway.

In another manufacture, the dosage form Is manufactured by the wet granulation technique. In the wet granulation technique, for example, the drug and the ingredients comprising the drug-forming layer are blended using a solvent, such as ethyl alcohol-water 98:2 v:v (volume:volume) as the granulation fluid. Other granulating fluid, such as denatured alcohol 100%, can be used for this purpose. The ingredients forming the drug layer are individually passed through a 20 mesh screen and then thoroughly blended in a mixer. Next, other Ingredients comprising the drug layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass than is forced through a 20 mesh screen onto oven trays. The blend is dried for 18 to 24 hours at 30° C. to 50° C. The dry g granules are sized then with a 20 mesh screen. Next, a lubricant is passed through screen, 'such as a 80-mesh screen, and added to the dry screen granule blend. The granulation is placed in a blender and blended for 1 to 15 minutes. A push layer is made by the same wet granulation techniques. The compositions are pressed into their individual layers in a layer press.

Another manufacturing process that can be used for providing the compartment-forming composition layers comprises blending the powdered ingredients for each layer independently in a fluid bed granulator. After the powdered are dry blended in the granulator, a granulating fluid, for example, poly(vinylpyrrolidone) in water, or in denatured alcohol, is sprayed on the powders. Optionally, the ingredients can be dissolved or suspended in the granulating fluid. The coated powders are then dried in a granulator. This process granulated all the ingredients present therein while added the granulating fluid. After the granules are dried, a lubricant such as stearic acid or magnesium stearate is added to the granulator. The granules for each separate layer are pressed then in the manner described above.

The dosage form of the invention can be manufactured by mixing a drug with composition-forming ingredients and pressing the composition into a layer possessing dimensions that correspond to the internal dimensions of the compartment of the dosage form. In another manufacture the drug and other drug composition-forming ingredients and a solvent are mixed into a solid, or a semisolid, by conventional methods such as ballmilling, shaking, calendaring, tumbling, stirring or rollmilling, and then pressed into a preselected layer-forming shape. Next, a layer of a composition comprising an osmopolymer and an optional osmagent are placed In contact the drug layer. The layering of the first layer comprising the drug and the second layer comprising the osmopolymer and optional osmagent composition can be accomplished by using a conventional layer press technique. The wall can be applied by molding, brushing, spraying or dipping the pressed bilayer's shapes with all-forming materials. another and preferred technique that can be used for applying the wall is the air-suspension coating procedure. This procedure consists in suspending and tumbling the two contacting layers in current of air until the wall-forming composition surrounds the layers. The air suspension procedure is described in U.S. Pat. No. 2,799,241; *J. Am. Pharm. Assoc.*, Vol. 48 pp 451–454 (1979); and, abid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1678 (1970), published by Mack Publishing Co., Easton, Pa.

Exemplary solvents suitable for manufacturing the wall, a single layer and a bilayer core include inert inorganic and organic solvents final laminated wall. The solvents broadly include a single solvent members selected for the group consisting of aqueous solvent, alcohol, ketone, ester, ether, aliphatic hydrocarbon, halogenated solvent, cyclaliphatic, aromatic, and hetercyclic solvents. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane ethylene glycol monoethyl ether, ethylene glycol monoethyl acetate, methylene dichloride, ethylene dichloride, propylene dichloride, carbon tetrachloride, chloroform, nitroethane, nitropropane, tetrachoroethan, ethyl ether, isopropyl ether, cyclohexane, cyclooctane, benzene, toluene, naptha, tetrahydrofuran, and diglyme.

The expression therapeutically active agent as used for the purposes of this invention includes a drug, or a composition comprising a therapeutically active drug and other composition forming ingredients the term drug includes any physiologically of pharmacologically active substance that produces a local or a systemic effect in animals including humans. The terms physiologically and pharmacologically are defined in *Stedman;s Medical Dictionary*, published by Williams and Wilkins, 1966, Baltimore, Md. The drug comprise a member selected from the group consisting of anticonvulsant, analgesic, anti-inflammatory, anesthetic, anti-Parkinson, antimicrobial, antimalerial, antiviral, antiparasitic, cardiovascular, contraceptive, central nervous system actant including depressant and stimulant, diuretic, electrolyte, hormone, hypoglycemic, muscle contractant, muscle relaxant, hypnotic, ophthalmic, psychic energizer, neoplastic, sedative, sympathomimetic, and tranquilizer. The drugs are know in *Pharmaceutical Sciences*, by Remington, 17th Edition, 1985, published by Mack Publishing Co., Easton, Pa.

The drug can be in various pharmaceutically acceptable form, such as uncharged molecules, molecular complexes, pharmacologically acceptable salts such as hydrochloride, hydrobromide, sulfate, laurylate, palmitate, phosphate, nitrate, borate, acetate, makeate, tartrate, oleate and salicylate. For acidic medicines salts of metals, amines organic cations; for example quatemary ammonium can be used. Derivatives of medicines, such as an ester, ether and amides, can be used. Also, a medicine that is water insoluble can be used in a form that is a water soluble derivative thereof to serve as a solute, and its release from a dosage form it is converted by enzymes, hydrolyzed by the body pH, or other metabolic process to the original biologically active form.

Representative of drug that can be administered by this invention include a member selected from the group consisting of simvastation sumatriptan, doxazosin, amlodipine, azithromycin, lisinopril, finasteride, ziprasidone, olanzapine, risperidone, sildenafil, dofetilide, donepezil, atorvastatin, trovafloxacin, eprosartan, losartan, tasosartan, enalapril, sertindole, quetiapine, nelfinavin, ritonavir, indinavir, dexlenfluramine, and citicolene, The dose of drug in a dosage form provided by the invention is 100 micrograms to 1000 milligrams.

DETAILED DESCRIPTION OF EXAMPLES OF THE INVENTION

The following examples are merely illustrative of the present invention and they should not be considered as limiting the scope of the invention in any way, as these examples and other equivalents thereof will become more apparent to those skilled in the drug delivery art in the light of the present disclosure, the drawings and the accompanying claims.

EXAMPLE 1

A series of osmotic therapeutic compositions comprising a dose of pentoxifylline were coated with a membrane-forming composition comprising 55 wt % of ethylcellullose having an ethoxyl content of 48.0 to 49.5 weight percent and a 220,000 molecular weight, 20 wt % of hydroxypropylcellulose of 60,000 molecular weight, 20 wt % of polyvinylpyrrolidone of 1,300 molecular weight and 5 wt % of polyoxyethylenated stearate comprising 40 moles of ethylene oxide. The wall-forming ingredients were dissolved with stirring in 100% anhydrous ethanol. Then, the freshly prepared coating solution was allowed to solvate as room temperature, 20° C., for 72 hours. The solvated solution was divided into two equal portions. One portion was spray coated on the therapeutic compositions without stirring the solution, and the other portion was stirred continuously while the coating was applied to the therapeutic composition. The performance curves of the resulting dosage forms were equivalent as seen in FIG. 1. Drawing FIG. 1 illustrates the release rate vs the reciprocal membrane weight for dosage forms sprayed at two coating conditions. The clear square indicates membranes formed unstirred while spraying and the dark squares indicates membranes formed while spraying the membrane forming composition. The core of the dosage form comprised a bilayer tablet therapeutic composition. One layer, the drug layer, weighed 845 mg and consisted of 71 wt % pentoxifylline, 24.67 wt % polyethylene oxide of 200,000 molecular weight, 4 wt % polyvinylpyrrolidone of 40,000 molecular weight, 0.25 wt % magnesium stearate and 0.08 wt % butylated hydroxytoluene. The dosage form comprises a push layer composition for pushing the therapeutic composition from the dosage form. The push layer composition weighed 200 mg and consists of 97.70 wt % polyethylene oxide of 5,000,000 molecular weight, 1 wt % polyvinylpyrrolidone of 40,000 molecular weight, 1 wt % ferric oxide, 0.25 wt % magnesium stearate, and 0.05 wt % butylated hydroxglotuene. The membrane comprises two round 25 mil (0.635 mm) diameter exits.

EXAMPLE 2

A series of therapeutic compositions were prepared for manufacturing into dosage forms for illustrating the unexpected improvements for the dosage forms of Example 1 over the dosage forms of Example 2. In Example 2, therapeutic compositions comprising pentoxifyllene were coated with a membrane composition comprising 55 wt % ethylcellulose of 220,000 molecular weight, 22.5 wt % hydroxypropylcellulose of 60,000 molecular weight and 22.5 wt % of polyethylene glycol of 8,000 molecular weight. The membrane was coated with a binary solvent system consisting of 3,477 ml of anhydrous ethanol and 47 ml of water. The membrane coating solution was prepared by dissolving the ethylcellulose and the hydroxypropylcellulose in the ethanol and the polyethylene glycol in water and then blending the two solutions to form the final coating solution. The polyethylene glycol was soluble in water and in the ethanol binary mixture, but not soluble in ethanol alone. The final coating solution comprised 98.3% ethanol and 1.7% water. A subsequent coating composition comprised 95% ethanol and 5% water. The two coating runs produced dosage form comprising membrane of distinct coating weights. The results of the measured performance of individual membrane dosage forms for two coating revealed the membranes which were formed with the coating revealed the membranes which were formed with the coating solutions having 5% water produced much faster release rate of drug than membranes of comparable weight coated with 1.7% water as seen in drawing FIG. 2. The wide divergence of these two performance curves demonstrated that small changes in the ratio of a binary solvent can produce significantly different permeabilities in membranes. For this binary system it makes the production of reproducible membrane very different because it is difficult to keep the ratio of solvents constant from batch to batch and from within a batch during the coating process.

Figure 2:
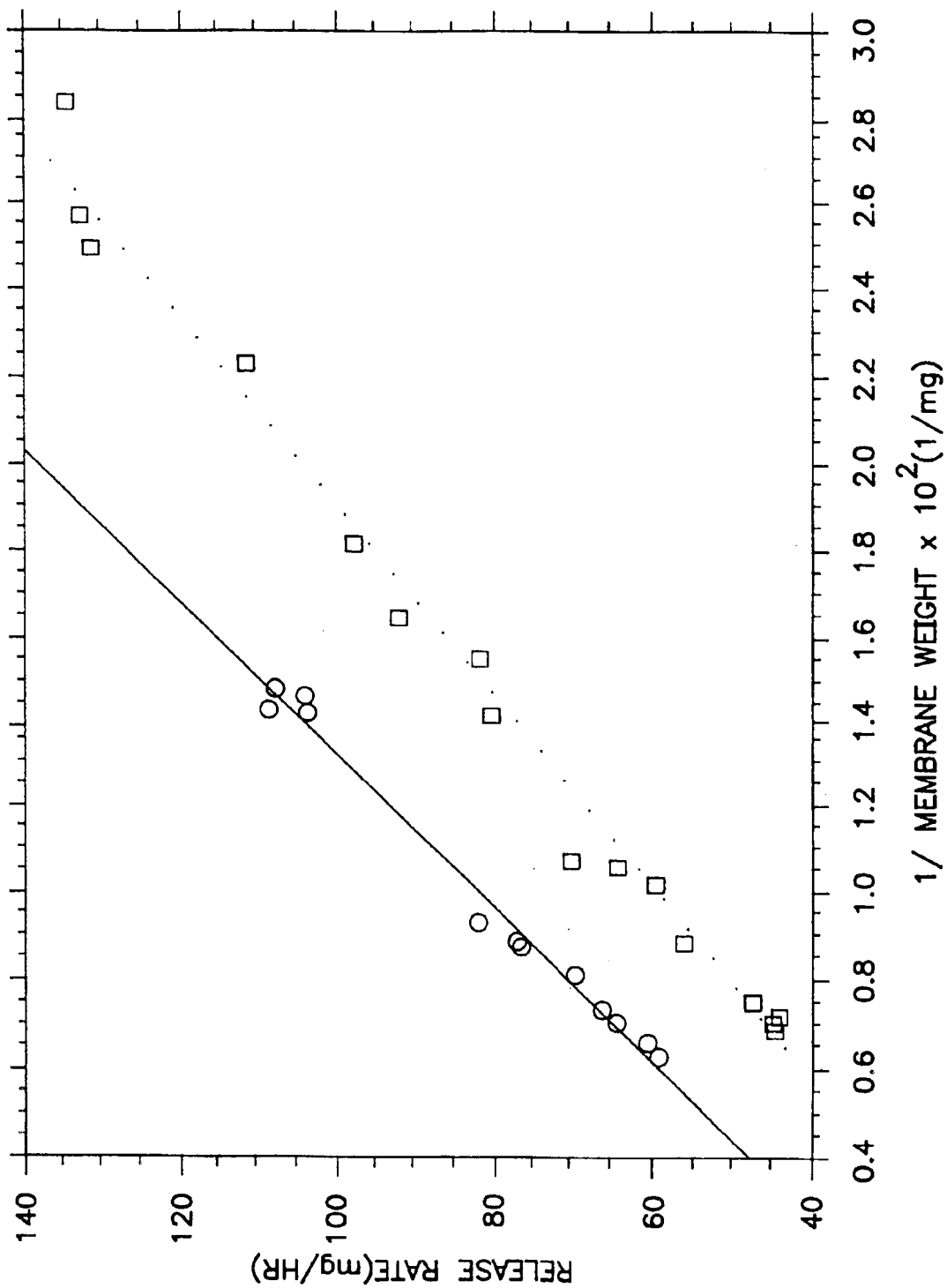
FIG. 2 depicts the release rate vs the reciprocal membrane weight sprayed from two ethanol/water ratios.

The accompanying drawing FIG. 2 illustrates the release rate vs reciprocal membrane weight for a series of dosage forms comprising ethylcellulose in the membrane. In the drawing FIG. 2, the clear circles represent a binary solvent comprising 95% ethanol and 5% water and the clear squares represent a binary solvent system comprising 98.3% ethanol and 1.7% water. The dosage form of Example 2, comprises a therapeutic composition weighing 845 mg and consisting of 71% pentoxifylline, 24.67 wt % polyethylene oxide of 200,000 molecular weight, 4 wt % polyvinyl-pyrrolidone of 40,000 molecular weight, 0.25 wt % magnesium stearate and 0.08 wt % butylated hydroxytoluene. The dosage form comprises a push composition in laminated arrangement with the therapeutic composition. The push composition weigh 200 mg and comprises 97.70 wt. % polyethylene oxide of 5,000,000 molecular weight, 1 wt % polyvinylpyrrolidone of 40,000 molecular weight, 1 wt % ferric oxide, 0.25 wt % magnesium stearate, and 0.05 wt % butylated hydroxytoluene. The release rate form the dosage forms were measured in artificial gastric juice at 37° C. The dosage form comprised two, 25 mil (0.635 mm) exit passageways in the membrane that connected the therapeutic composition with the exterior of the dosage form.

EXAMPLE 3

Figure 3:
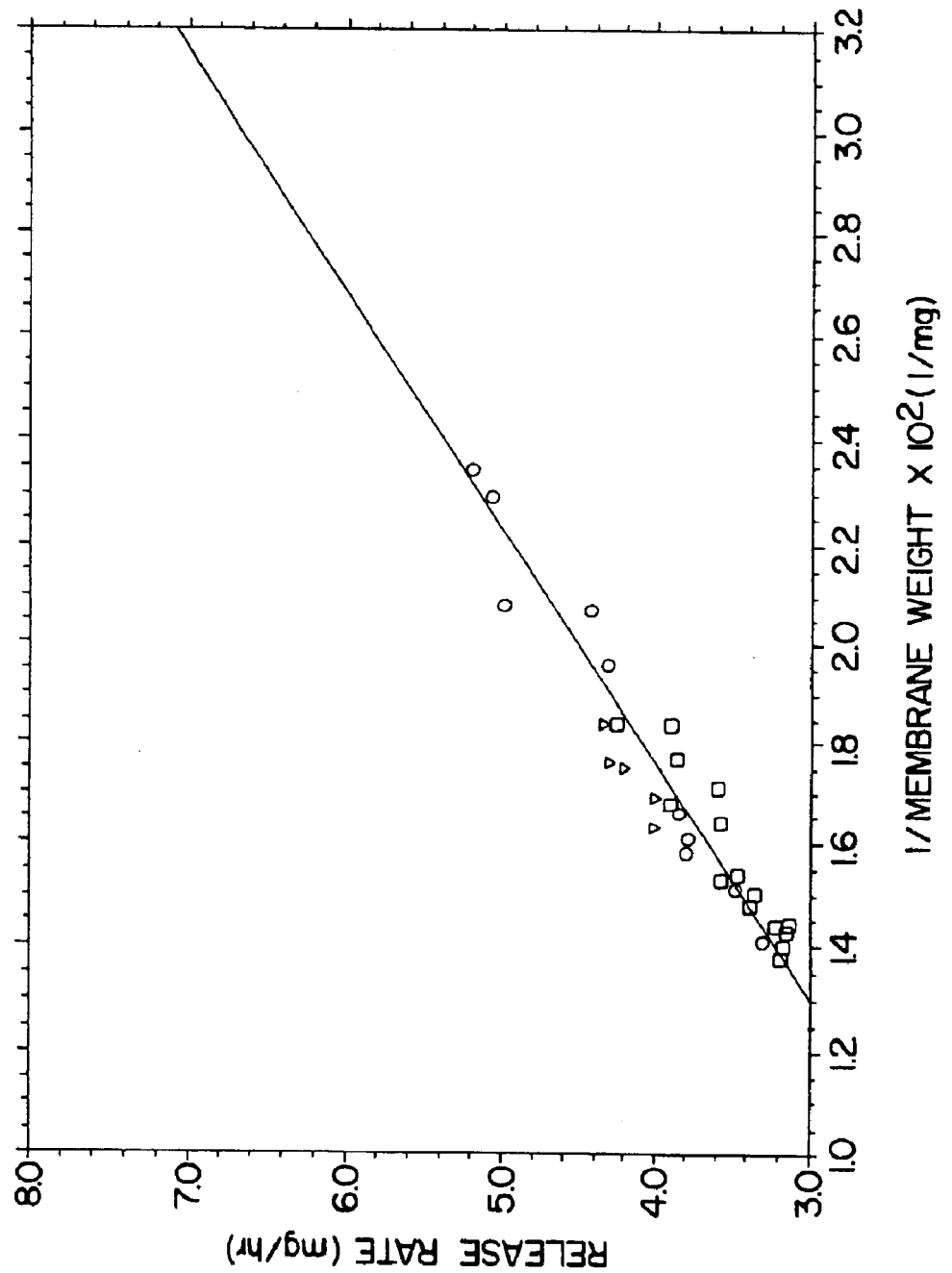
FIG. 3 depicts a membrane surfactant composition coated from a single solvent from three coating runs.

The procedure of Example 1 is followed in this example. In this example, the therapeutic composition is coated with a membrane composition consisting of 79 wt % cellulose acetate comprising 39.8% acetyl content having molecular weight of 40,000 and 21 wt % of a surfactant comprising 30 wt % polyoxypropylene glycol having a 8,400 molecular weight and 160 moles of ethylene oxide. The coating solution was prepared by dissolving the cellulose acetate and polyoxypropylene glycol in the single solvent with stirring and slight warming to 30° C. The membrane was sprayed from a single solvent consisting of 100% acetone, and the membranes formed from the coating composition was smooth, without cracks or cusps. The uniform morphology for these dosage forms is seen in accompanying drawing FIG. 3 showing the performance of the membrane coating. Drawing FIG. 3 depicts the results for a drug composition weighing 319 mg consisting of 35 % tacrine hydrochloride, 57 wt % mannitol, 3 wt % hydroxypropylmethyl-cellulose of 9,200 molecular weight, 1 wt % polyvinylpyrrolidone of 40,000 molecular weight, 3 wt % crosslinked polyvinylpyrrolidone, I wt % magnesium stearate which composition is surrounded by the membrane. The dosage form comprises two 10 ml (0.254 mm) exit passageways for releasing the drug from the dosage form. In drawing FIG. 3, the clear circles, triangles and squares depict the release pattern for these lots of dosage forms, with each symbol type representing each of three lots. The figure illustrates the data is clustered together, indicating good reproducibility. The morphology of the membranes when observed in cross section under microscopic examination was smooth, without cracks, laminations, striations, or cusps.

EXAMPLE 4

Figure 4:
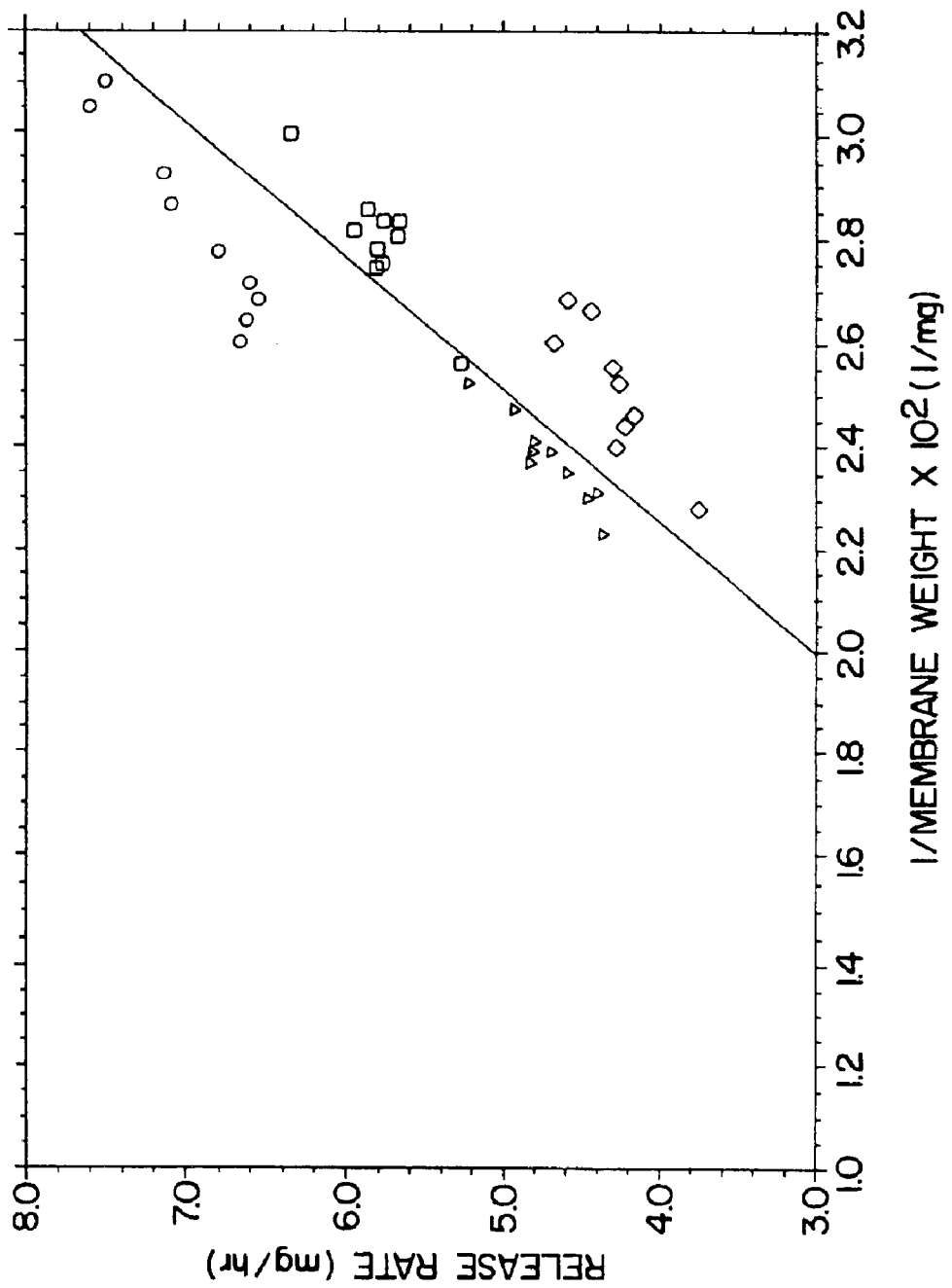
FIG. 4 depicts membranes coated from a binary solvent from four coating runs.

Therapeutic compositions comprising tacrine hydrochloride were coated with a membrane-forming composition comprising 75 wt % cellulose acetate comprising a 39.8% acetyl content and having a molecular weight of 40,000, 23 wt % polyvinylpyrrolidone and having a molecular weight of 40,000, and 2 wt % triethylcitrate. The membrane-forming ingredients were dissolved in a binary solvent comprising 80/20 (wt/wt) acetone/methanol. The therapeutic compositions were coated with the membrane and the performance is depicted in drawing FIG. 4. In drawing FIG. 4, the drug composition coated with the membrane weighed 321.3 mg, and consisted of 34 wt % tacrine hydrochloride, 60 wt % mannitol, 3 wt % hydroxypropylmethyl-cellulose of 9, 200 molecular weight, 1 wt % polyvinylpyrrolidone of 40,000 molecular weight, 1 wt % cross-linked sodium carboxymethylcellulose, and 1 wt % magnesium stearate. The dosage form is comprises two 10 mil (0.254 mm) exit orifices. In drawing FIG. 4, the clear circles, triangles, squares and diamonds illustrate different dosage forms release rate analyzed with 10 dosage forms in each of four lots. Each type of symbol represents one lot. FIG. 4 depicts the dosage forms prepared by using the binary solvent exhibited unacceptable performance as the reproducibility was poor. The morphology of the membranes under microscopic examination evidence ranged from homogenous to very heterogenous. The heterogenous structures were characterized as being laminar, with striations, cracks, and cusps within the membrane structure.

EXAMPLE 5

In this example, ten surfactant flux enhancers were evaluated by coating 70/30 cellulose acetate/enhancer blends from 100% acetone. The permeability values of the surfactant enhancer are summarized in Table 1. The Pluronic F68 compound produced the highest permeability value. It also produced membranes which had the most uniform morphology when examined in cross section under microscopic examination.

Samples of the membrane were soaked from coated cores and tested for tensile properties. A miniature dogbone shaped steel rule die was used to punch out samples for testing. The dogbone-shaped samples were pulled on tensile tester. The modulus of elasticity, elongation at break, and toughness values for the 70/30 cellulose acetate/Pluronic F68 membrane were high; 59 kgf/mm2, 23%, and 0.3 kgf/mm2, respectively.

Therefore, this membrane which was formulated with a surfactant flux enhancer and sprayed from a single solvent had a high water permeability value, had good mechanical properties, and was reproducible.

TABLE 1

| Surfactant Enhancer | Melting Point (° C.) | Mol. Wt (g/mole) | Permeability (k × $10^4$) (cm.mil/atm.hr) |
|---|---|---|---|
| Myrj 52S | 38 | 2,047 | 10.7 |
| Myrj 53 | 42 | 2,487 | 13.2 |
| Tween 20 | <25 | 1,126 | 9.3 |
| Tween 40 | 13 | 1,282 | 6.5 |
| Tween 80 | <25 | 1,309 | 6.2 |
| Luviskol VA37E | 67($T_g$) | 45,000 | 2.2 |
| Luviskol VA64P | 106($T_g$) | 44,000 | 7.1 |
| Pluronic F68 | 52 | 8,600 | 15.4 |
| Pluronic F108 | 57 | 14,600 | 12.3 |
| Pluronic F127 | 56 | 12,600 | 10.5 |

In Table 1, Myrj® 52s denoted polyoxyethylenated stearic acid with 40 moles of ethylene oxide; Myrj® 53 denotes polyoxyethylenated stearic acid with 50 moles of ethylene oxides; Tween® 20 denotes polyoxyethylenated sorbitan monolaurate with 20 moles of ethylene oxide; Tween 40 denoted polyoxyethylenated sorbitan monopalmitate with 20 moles of ethylene oxide; Tween 80 denotes polyoxyethylenated sorbitan monoleate and 20 moles of ethylene oxide; Luviskol® VA 37E denotes vinylpyrrolidone/vinyl acetate copolymer with 30 wt % of vinylpyrrolidone and 70 wt % of vinylacetate; Luviskol® VA 64P denotes vinylpyrrolidone/vinyl acetate copolymer with 60 wt % vinylpyrrolidone and 40% vinyl acetate having a molecular weight of approximately 60,000; Pluronic® F68 denotes polyoxypropylene glycol of 8,600 molecular weight and 160 moles of ethylene oxide; Pluronic® 108 denotes polyoxypropylene glycol of 14,600 molecular weight and 280 moles of ethylene oxide; and Pluronic® 127 denotes polyoxypropylene glycol of 12,600 molecular weight and 200 moles of ethylene oxide. The Myrij and Tween products are commercially available from the ICI Americas, Inc., Wilmington, Del. The Pluronic and Luviskol products are available from BASF Corporation, Mt. Olive, N.J.

In as much as the foregoing specification comprises present embodiments of the invention, it is understood, variations and modifications can be made, in accordance with the disclosed invention, without departing from the scope of the invention.

We claim:

1. A composition consisting essentially of:
    a combination of ethylcellulose and amphiphilic triblock copolymer surfactant, wherein the amphiphilic triblock copolymer surfactant consists of a triblock copolymer of ethylene oxide-propylene oxide-ethylene oxide and the composition in dry coated form includes 40 wt % to 99.5 wt % ethyl cellulose and 0.5 wt % to 60 wt % of the amphiphilic triblock copolymer surfactant; and
    a single organic solvent, wherein the ethyl cellulose and the amphipilic triblock polymer surfactant are each dissolved in the single organic solvent.

2. The composition according to claim 1, wherein the molecular weight of the amphiphilic triblock copolymer surfactant is 2,200 to 15,000.

3. The composition of claim 1, wherein the ethylene oxide-propylene oxide-ethylene oxide triblock copolymer comprises, on a molar basis, 3 to 20 moles of ethylene oxide.

4. The composition of claim 1, wherein the ethylene oxide-propylene oxide-ethylene oxide triblock copolymer comprises, on a molar basis, 45 to 80 moles of ethylene oxide.

5. The composition of claim 1, wherein the ethylene oxide-propylene oxide-ethelene oxide triblock copolymer comprises, on a molar basis, 50 to 110 moles of ethylene oxide.

6. The composition of claim 1, wherein the ethylene oxide-propylene oxide-ethelene oxide triblock copolymer comprises, on a molar basis, 70 to 130 moles of ethylene oxide.

7. The composition of claim 1, wherein the ethylene oxide-propylene oxide-ethelene oxide triblock copolymer comprises, on a molar basis, 110 to 170 moles of ethylene oxide.

* * * * *